US009643988B2

(12) United States Patent
Lichtenberger et al.

(10) Patent No.: US 9,643,988 B2
(45) Date of Patent: May 9, 2017

(54) COMPOUNDS HAVING LOW IONIZATION ENERGY

(71) Applicant: THE ARIZONA BOARD OF REGENTS ON BEHALF OF THE UNIVERSITY OF ARIZONA, Tucson, AZ (US)

(72) Inventors: Dennis Lichtenberger, Tucson, AZ (US); Carlos Murillo, College Station, TX (US)

(73) Assignee: The Arizona Board of Regents on behalf of the University of Arizona, Tucson, AZ (US)

( * ) Notice: Subject to any disclaimer, the term of this patent is extended or adjusted under 35 U.S.C. 154(b) by 0 days.

(21) Appl. No.: 14/490,628

(22) Filed: Sep. 18, 2014

(65) Prior Publication Data
US 2015/0080571 A1    Mar. 19, 2015

Related U.S. Application Data

(60) Provisional application No. 61/880,135, filed on Sep. 19, 2013.

(51) Int. Cl.
*C07F 11/00* (2006.01)
*B01J 31/22* (2006.01)
*C07D 487/04* (2006.01)

(52) U.S. Cl.
CPC ........... *C07F 11/00* (2013.01); *B01J 31/2295* (2013.01); *C07D 487/04* (2013.01); *C07F 11/005* (2013.01); *B01J 2231/005* (2013.01); *B01J 2531/66* (2013.01)

(58) Field of Classification Search
CPC ............................. C07F 11/00; B01J 31/2295
USPC ....................................................... 544/181
See application file for complete search history.

(56) References Cited

U.S. PATENT DOCUMENTS 4,797,487 A    1/1989    A'Court

FOREIGN PATENT DOCUMENTS

FI    82445    11/1990

OTHER PUBLICATIONS

Moore, C. E., "Ionization Potentials and Ionization Limits Derived from the Analysis of Optical Spectra," NSRDS-NIBS 34, National Bureau of Standards, Washington, DC, 1970.
Foley, S. R. et al., Polyhedron 2002, 21, 619-627.
Soria, D. B. et al., J. Organometal. Chem. 2005, 690, 2278-2284.
Coles, M. P. et al., Organometallics 2003, 22, 5201-5211.
Coles, M. P. et al., Dalton Trans. 2001, 1169-1171.
Coles, M. P. et al., Inorg. Chim. Acta 2004, 357, 4330-4334.
Oakley, S.H. et al., Inorg. Chem. 2004, 43, 7564-7566.
Doles, Mp., et al., Eur. J. Inorg. Chem. 2004, 2662-2672.
Irwin, M. D. et al., Chem. Commun. 2003, 2882-2883.
Feil, F. et al., Eur. J. Inorg. Chem. 2005, 4438-4443.
Wilder, C. B. et al., Inorg. Chem. 2006, 45, 263-268.
Rische, D. et al., Inorg. Chem. 2006, 45, 269-277.
Duncan, A. P. et al., Organometallics 2001, 20, 1808-1819.
Edelmann, F.T., Chem. Soc. Rev. 2009, 38, 2253-2268.
Chiarella, G. M. et al., Chem. Commun. 2010, 46, 136-138.
Lee, R. et al., Dalton Trans. 2010, 39, 723-725.
Ciabanu, O. et al., Anorg. Allg. Chem. 2010, 636, 543-550.
Zheng, P. et al., Organometallics 2010, 29, 1284-1289.
Fu, X. et al., Chem. Commun. 2011, 47, 8210-8222.
Wild, U. et al., Eur. J. Inorg. Chem. 2011, 4220-4233.
Li, L. et al., J. Org. Chem. 2003, 68, 8786-8789.
Deutsch, J. et al., Tetrahedron 2009, 65, 10365-10369.
Schulenberg, N. et al., Eur. J. Inorg. Chem. 2010, 5183-5188.
Colton, F. A. et al., Inorg. Chem. 2006, 45, 201-213.
Vannucci, A. K et al., Inorg. Chem., 2009, 48, 8856-8862.
Ryan, M. F. et al., Organometallics 1994, 13, 1190-1199.
Cotton, F. A. et al., Inorg. Chem. Commun. 2003, 6, 121-126.
Chiarella, G. M. et al., Polyhedron 2013, 58, 7-12.
Cotton, F. A. et al., J. Chem. Phys. B 2006, 110, 19793-19798.
Lichtenberger, D.L. et al., Rev. Sci. Instrum. 1986, 57, 2366.
Westcott, B. L. et al., J. Am. Chem. Soc. 1998, 120, 3382-3386 and references therein.
Van Der Sluis, P. et al., Acta Cryst. 1990, A46, 194-201.
Spek A. L., "Single-crystal structure validation with the program PLATON," J. Appl. Cryst. (2003). 36, 7-13.
Marsh, R. E., Acta Crystallogr. 2009, B65, 782-783.
Te Velde, G. et al., J. Comp. Chem. 2001,22, 931-967.
Fonseca Guerra, C. et al., Theor. Chem. Acc. 1998, 99, 391-403.
Grimme, S. et al., J. Comp. Chem. 2011, 32, 1456-1465.
Perdew, J. P. et al., Phys. Rev. Lett. 1996, 77, 3865.
Van Lenthe, E. et al., J. Chem. Phys. 1994, 101, 9783-9792.
Klamt, A., J. Phys. Chem. 1995, 99, 2224-2235.
Vosko, S. H. et al., Can. J. Phys. 1980, 58, 1200-1211.
Stoll, H. et al., Theor. Chim. Acta 1978, 49, 143-149.
Li, H. et al., Inorg. Chem. 2012, 51, 5716-5727.

*Primary Examiner* — Paul V Ward
(74) *Attorney, Agent, or Firm* — Don D. Cha; Hamilton DeSanctis & Cha, LLP.

(57) ABSTRACT

The present invention provides compounds that are soluble in a non-polar solvent and having a low ionization energy and negative oxidation potentials in tetrahydrofuran (THF). The present invention also provides a method for producing and using the same.

20 Claims, 2 Drawing Sheets

COMPOUNDS HAVING LOW IONIZATION ENERGY

CROSS-REFERENCE TO RELATED APPLICATIONS

This application claims the priority benefit of U.S. Provisional Application No. 61/880,135, filed Sep. 19, 2013, which is incorporated herein by reference in its entirety.

STATEMENT REGARDING FEDERALLY FUNDED RESEARCH

This invention was made with government support under grant number CHE-1111570 awarded by the National Science Foundation. The government has certain rights in the invention.

FIELD OF THE INVENTION

The present invention relates to a compound that is soluble in a non-polar solvent and/or having a low ionization energy, negative oxidation potentials in tetrahydrofuran (THF, e.g., versus ferrocene/ferrocenium), or both. The present invention also relates to a method for producing and using the same.

BACKGROUND OF THE INVENTION

The phenomena of oxidation (electron loss) and reduction (electron gain) are fundamental to chemistry. Even when these processes do not occur as such, more complex chemical processes and properties, such as ionic and covalent bond formation and acid-base behavior, can be understood by including them as a sum of oxidation and/or reduction steps. Tables of oxidation enthalpies, electron affinities, and electrode (redox) potentials are essential to understanding and teaching chemistry Stable, strong oxidizing and reducing agents have many important chemical and materials applications. Especially needed are strong redox agents to be utilized in non-aqueous, homogeneous systems. While strong redox agents have recently been developed, including by the present inventors, many of these compounds are not soluble in nonpolar and/or aprotic solvents, thereby rendering them virtually useless in chemical reactions requiring nonpolar and/or aprotic solvent.

Therefore, there is a need for strong redox agents that are soluble in nonpolar and/or aprotic solvents.

SUMMARY OF THE INVENTION

Some aspects of the invention provide compounds comprising a metal and an organic ligand. In some embodiments, the compounds of the invention have a low ionization energy and negative oxidation potential on the electrochemical scale. Therefore, compounds of the invention are useful in a wide variety of applications including, but not limited to, as reducing agents, catalysts, in solar cells, in electronics (such as capacitors, light emitting diodes, etc.), in nanoparticles, etc. The compounds of the invention can also be used in hydrogen production, as well as catalysts in solar fuel production. In general, compounds of the invention can be used in any applications that utilize a compound having a low ionization energy and negative oxidation potential.

In some embodiments, the onset ionization energy of the compound of the invention is about 4 eV or less, typically 3.8 eV or less, often 3.6 eV or less, and more often 3.5 eV or less.

Yet in other embodiments compounds of the invention are soluble in an aprotic organic solvent. Exemplary aprotic organic solvents include, but are not limited to, diethyl ether, tetrahydrofuran (THF), dimethylsulfoxide (DMSO), benzene, toluene, methylene chloride, chloroform, acetonitrile, ethyl acetate, acetone, hexane, pentane, 1,4-dioxane, dimethylformamide (DMF), etc.

Still in other embodiments, compounds of the invention are soluble in a nonpolar organic solvent. As used herein, the term "nonpolar" refers to a solvent having a dielectric constant of about 10 or less, typically 8 or less, often 7 or less, and more often 5 or less. Exemplary nonpolar organic solvents include, but are not limited to, pentane, hexane, cyclohexane, benzene, toluene, 1,4-dioxane, chloroform, diethyl ether, etc.

Yet in other embodiments, compounds of the invention have an oxidation potential in THF of about 0.0 V or less, typically −1.5 V or less, often −1.8 V or less versus ferrocene/ferrocenium.

The solubility of compounds of the invention in THF is at least 0.1 g/L, typically at least 0.5 g/L, often at least 1 g/L, more often at least 2 g/L, and most often at least 5 g/L. The solubility of compounds of the invention are typically determined under standard conditions, e.g., 20° C. at 1 atmosphere of pressure.

In some embodiments, the solubility of compounds of the invention in benzene is at least 0.1 g/L, typically at least 0.5 g/L, often at least 1 g/L, more often at least 2 g/L, and most often at least 5 g/L.

In some embodiments of the invention, the compound of the invention is a tungsten compound of the formula:

where L is an anionic organic ligand, X is a halide, and m is an integer from 0 to 2. As used herein, unless the context requires otherwise the terms "anionic organic ligand" and "organic ligand" are used interchangeably herein and refer to a ligand that comprises hydrocarbons. Hydrocarbon can be saturated, unsaturated, linear, cyclic (e.g., mono-cyclic, bicyclic, tricyclic, etc.) or a combination thereof. The organic ligand can also include a heteroatom selected from the group consisting of N, O, S, or P. In some embodiments, the anionic organic ligand is a bicyclic heterocycloalkyl. Yet in other embodiments, the anionic organic ligand is a bicyclic heterocycloalkyl comprising one to five, typically one to four, often one to three heteroatom that is independently selected from the group consisting of N, O, S, and P.

Still in other embodiments, each L is nitrogen atom containing bicyclic heteroalkyl, where the number of nitrogen atom in the cyclic ring structure ranges from one to five, typically one to four, and often one to three. In one particular embodiment, each L is independently alkyl substituted guanidinate. As used herein, the term "alkyl" refers to a saturated linear monovalent hydrocarbon moiety or a saturated branched or cyclic monovalent hydrocarbon moiety. Optionally, one or more of the hydrogen atom in the alkyl group may be replaced with a halide such as chloro, bromo, fluoro or iodo. Furthermore, one or more of the carbon atom in the alkyl chain may be replaced with a heteroatom such as O, N, S or P. Suitable alkyl substituents for guanidinate include $C_1$-$C_{20}$ alkyl, typically $C_1$-$C_{12}$ alkyl, often $C_1$-$C_8$ alkyl, and more often $C_1$-$C_4$ alkyl. Typically, each L has at least one alkyl substituent, typically at least two alkyl substituents, often at least three alkyl substituents, and more often at least four alkyl substituents. Exemplary alkyl substituents include, but are not limited to, methyl, ethyl, propyl, isopropyl, butyl, sec-butyl, isobutyl, tert-butyl, pentyl, methoxymethyl, methoxyethyl, trifluoromethyl, trichloromethyl, chloromethyl, and the like. It should be appreciated that in some instances, L can be a chiral ligand, and therefore, the scope of the invention also includes enantiomerically enriched compound (i.e., a compound having an enantiomerically enriched L group(s)). As used herein, the term "guanidinate" refers to a moiety having 1,3,4,6,7,8-hexahydro-2H-pyrimido[1,2-a]pyrimidine structure and its derivatives.

In one particular embodiment of the invention, the compound of the invention is $W_2L_4$.

Still in other embodiments, each L is independently a moiety of the formula:

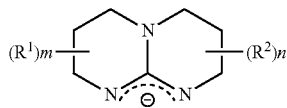

where each of m and n is independently an integer from 0 to 4, typically 0 to 3, provided the sum of m and n is at least 1, typically at least 2, often at least 3, and more often at least 4; each of $R^1$ and $R^2$ is independently alkyl, typically $C_1$-$C_{12}$ alkyl, often $C_1$-$C_{10}$ alkyl, more often $C_1$-$C_8$ alkyl, and most often $C_1$-$C_6$ alkyl. In one particular instance, n is 4. Still in other instances, each of $R^1$ and $R^2$ is independently methyl, ethyl, or $C_3$ or $C_4$ alkyl. In one particular embodiment, m and n are 2. Still in other embodiment, each of $R^1$ and $R^2$ is methyl or ethyl.

Yet in other embodiments, compounds of the invention are thermally stable and easy to synthesize in high yields and good purity. They are very reactive and potentially useful stoichiometric reducing agents in non-polar, non-protonated solvents.

Still further, combinations of the various embodiments described herein form other embodiments. For example, in one particularly embodiment $R^1$ and $R^2$ are ethyl, and m and n are 2. In this manner, a variety of compounds are embodied within the present invention.

DETAILED DESCRIPTION OF THE INVENTION

Figure 1:
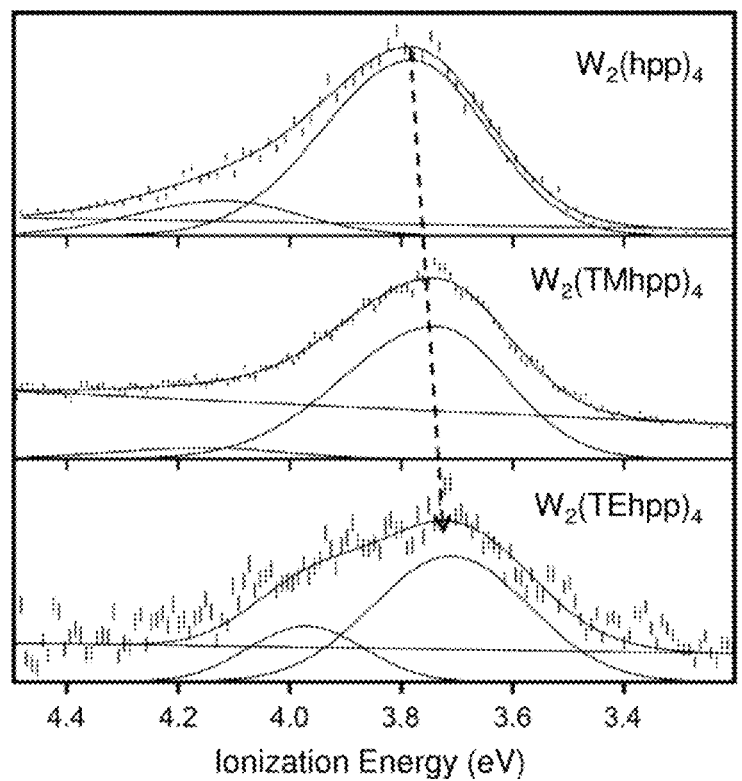
FIG. 1 is a photoelectron spectra of the low ionization energy regions (δ bond ionizations) of $W_2$(bicyclic guanidinate)$_4$ complexes.

Stable, strong oxidizing and reducing agents have many important chemical and materials applications. Especially needed are strong redox agents that are soluble in non-aqueous, nonpolar or aprotic solvent. As used herein, the term "soluble" refers to a compound that has solubility of at least 0.1 g/L, typically at least 0.25 g/L, often at least 0.5 g/L more often at least 1 g/L, still more often at least 2 g/L, and most often at least 5 g/L in THF. Thus, compounds of the invention allow homogeneous systems for carrying out a chemical reaction in a non-polar and/or aprotic organic solvent.

Some aspects of the invention are based on the discovery by the present inventors that compounds with metal-metal bonds with an anionic organic ligand (e.g., a bridging bicyclic guanidinate ligand) can often stabilize dimetal units in high oxidation states. In some cases, the common $M_2^{4+}$ units (where each M is independently a metal selected from the group consisting of tungsten or chromium) become extremely thermodynamically unstable to oxidation, the prime example being $W_2$(hpp)$_4$ (see below for ligand representations for "hpp", "TMhpp" and "TEhpp"). With an onset ionization energy of only 3.51 eV, this quadruple bonded $W_2$(hpp)$_4$ compound has the lowest known ionization energy for any molecule prepared in a synthesis laboratory, being even lower than that of cesium, the most easily ionized stable element.

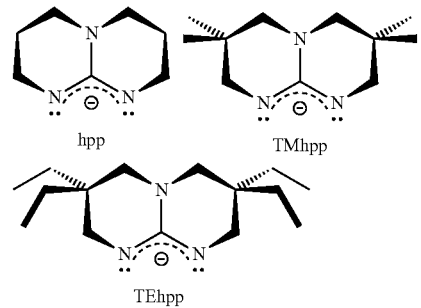

The redox properties of $W_2$(hpp)$_4$ and its ability to act as a reducing agent were investigated generating mixed results. This compound was found to be very reactive as a reductant, but a major drawback was the poor solubility in non-reactive organic solvents. Some aspects of the invention are based on the discovery by the present inventors that the derivative of hpp ditungsten compound has a significantly higher solubility in non-polar and/or aprotic organic solvent. Thus, by adding alkyl substituents to the hpp backbone, the present inventors have discovered that the resulting compounds have lower ionization energies and induce shifts in the negative direction in the oxidation potentials as well as increased solubility.

As described above, compounds of the invention have a low ionization energy and/or negative oxidation potentials. Furthermore, compounds of the invention are soluble in non-polar and aprotic solvents such as tetrahydrofuran (THF), benzene and other nonpolar solvents. Some of the compounds of the invention will now be described with reference to synthesis and characterization of a compound with triple bonded $W_2^{6+}$ cores, namely $W_2$(TMhpp)Cl$_2$, 1, and $W_2$(TEhpp)$_4$Cl$_2$, 2, that serve as precursors for the syntheses of $W_2$(TMhpp)$_4$, 3, and $W_2$(TEhpp)$_4$, 4, respectively. Compounds 1-3 have been characterized by X-ray crystallography and either electrochemical properties, photoelectron spectroscopy (PES), or other spectroscopic and spectrometric techniques and compound 4 has been characterized by $^1$H NMR and PES. The molecules have excellent properties for strong reducing agents in organic solvents.

The photoelectron spectra (FIG. 1) of the first ionization bands of compounds 3 and 4 revealed that the ionization energies ("IE") vary slightly but are lower than the ionization energy of the parent compound $W_2(hpp)_4$. The onset ionization energies ($IE_{onset}$) for the parent compound is 3.51±0.05. $IE_{onset}$ for compounds 3 and 4 was determined to be 3.45±0.03 and 3.40±0.05 eV, respectively, making compounds 3 and 4 as compounds with the lowest IEs known to date. For comparison, the IE for cesium is 3.89 eV. The IE for 3 was measured in the temperature range from 216 to 271° C. over a period of 2½ h while that for 4 was measured in the temperature range of 317-340° C. for about 1 h. In neither case was there any evidence of decomposition. This indicates that the thermal stability of both compounds in a vacuum is very high. As solids these species are almost indefinitely stable when stored in sealed ampoules protected from air and from protonated or halogenated solvents.

Figure 2:
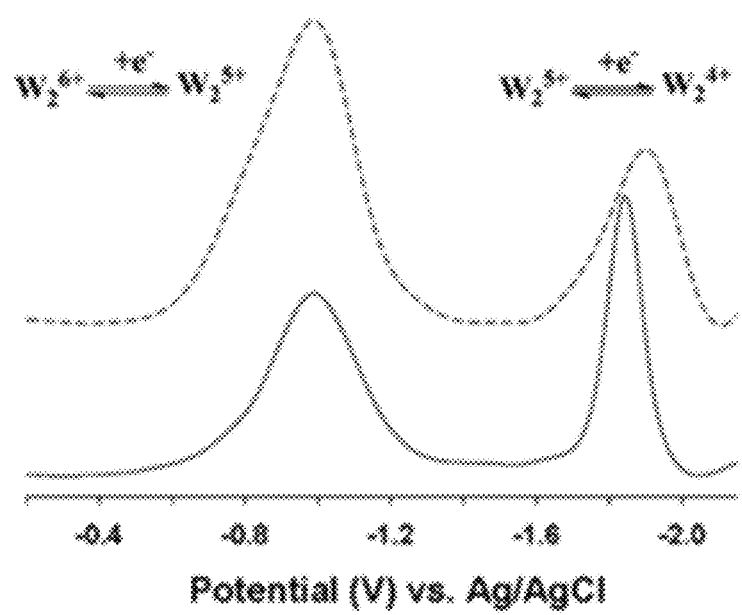
FIG. 2 is a differential pulse voltammograms in THF for $W_2Cl_2$(TMhpp)$_4$ (solid line) and $W_2Cl_2$(TEhpp)$_4$ (broken line).

Electrochemical measurements in THF of compounds 1 and 2 showed that each compound has two reversible redox waves at negative potentials. In the differential pulse voltammograms (DPVs, FIG. 2), the peaks at −1.84 and −1.90 V vs. Ag/AgCl have been assigned to the $W_2^{5+/4+}$ processes for the methyl and ethyl derivatives, respectively, and those at −0.99 and −0.99 V correspond to the $W_2^{6+/5+}$ processes. As a comparison, the reported $E_{1/2}$ of compound $W_2(hpp)_4$ is −0.97 V and −1.81 V for $W_2^{6+/5+}$ and $W_2^{5+/4+}$, respectively. The shifts in the solution oxidation potentials for these molecules are the same as the shifts of the onset gas phase IEs within experimental uncertainty, indicating that the solvation and thermodynamic effects on the relation between the ionization energies and oxidation potentials are similar for these molecules.

As shown in Scheme 1 below, compounds of the invention can be easily prepared in good yields using standard Schlenk-type techniques by reaction of commercially available and stable $W(CO)_6$ with the neutral bicyclic guanidinates in refluxing o-dichlorobenzene. The chlorinated solvent is useful not only in providing a high reflux temperature but also to serve as the oxidizing agent and be the source of the chlorine atoms in 1 and 2. Both compounds 1 and 2 can be handled in dry air over hours when they are in crystalline form. This makes them convenient sources for weighing and general handling of the compounds previous to further reactions. Compounds 1 and 2 can be readily reduced to compounds 3 and 4, respectively, for example, by treating with excess potassium metal in refluxing THF. The excess potassium metal can be removed by filtration, and the THF can be removed to obtain compounds 3 and 4. Removal of the THF solvent removes essentially a quantitative yield of the products. Further purification can easily be accomplished by removing the THF solvent followed by extraction with benzene or toluene.

Scheme 1

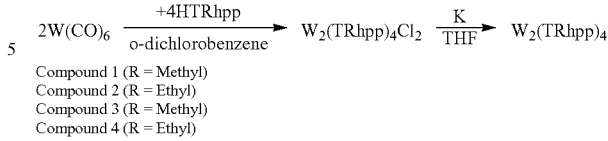

Compound 1 (R = Methyl)
Compound 2 (R = Ethyl)
Compound 3 (R = Methyl)
Compound 4 (R = Ethyl)

The present inventors have discovered that compounds 3 and 4 are very soluble in common dry solvents such as THF, toluene, and benzene. Some solubility of compound 3 in hexanes is also observed while compound 4 is significantly more soluble in the latter. In general, as the chain length of the alkyl substituent in the guanidinate increases, the higher the solubility in non-polar and/or aprotic solvent was observed.

The solubility properties of compounds 3 and 4 compare very favorably to those of decamethylcobaltocene, a commonly used reducing agent, but it is worth noting that the IEs and electrode potentials of compounds 3 and 4 are significantly more favorable than those of $(Cp^*)_2Co$. The ionization energy of $(Cp^*)_2Co$ at 4.705 eV is more than 1 eV greater than that of compounds 3 and 4, and the oxidation potential of $(Cp^*)_2Co$ at −1.47 V is approximately 0.4 V less negative than that of compounds 3 and 4.

Figure 3:
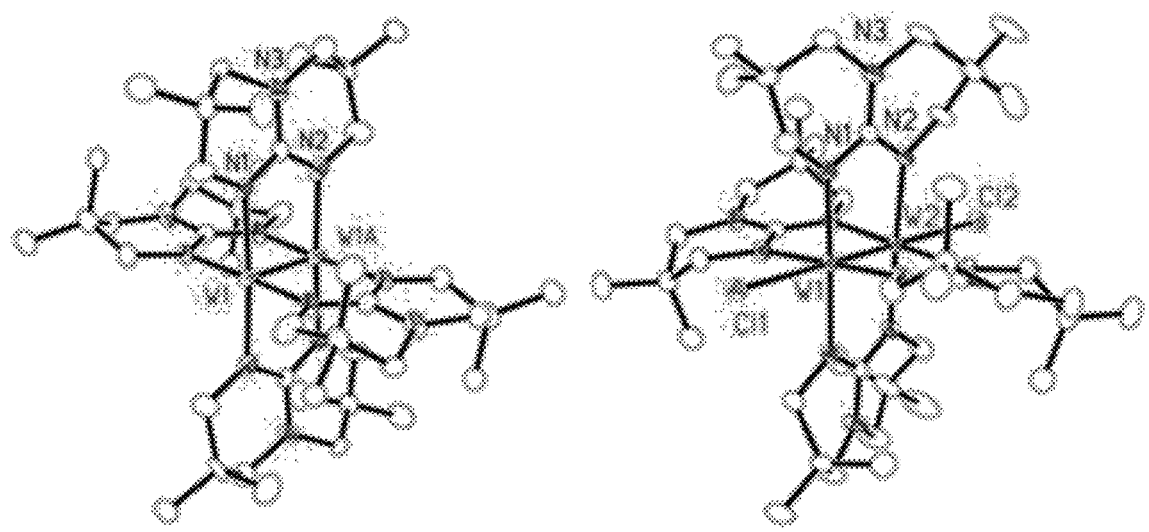
FIG. 3 is the representative structures of compound 1·4CH$_2$Cl$_2$ on the right and compound 3 on the left with displacement ellipsoids drawn at the 30% probability level. Solvent molecules in compound 1 and all hydrogen atoms have been removed for clarity.

The structures of compounds 1 and 3 (FIG. 3) show a paddlewheel structure with four bicyclic guanidinate ligands spanning the ditungsten unit. For compounds 1 and 2, it appears the chlorine atoms occupy axial positions at distances of about 2.98 Å and 2.85 Å, respectively. The 2.98 Å distance is the longest of over 3500 W—Cl distances found in the CCDC, and far beyond the mean of 2.42 Å, indicating only weak W—Cl bonding. Without being bound by any theory, the weakness of this bond is believed to be a contributing factor to the electrochemical properties of compounds of the invention.

Scheme 2

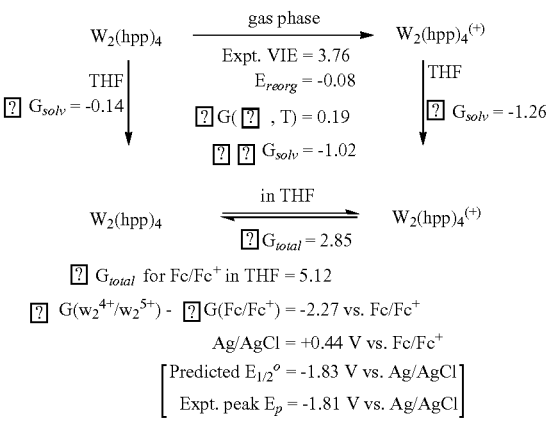

Photoelectron spectroscopy showed that ditungsten tetraguanidinate molecules of the invention give up electrons at extremely low ionization energies, e.g., around 3.4-3.5 eV. A closer examination of the connection between the ionization energies and the reduction potentials generally provides a better understanding of the strong reducing ability of these dimetal tetraguanidinate molecules in nonpolar organic solvents. Scheme 2 shows the connection starting from the experimental gas-phase vertical ionization energy (VIE or $IE_{vertical}$) of $W_2(hpp)_4$ shown in blue (i.e., VIE of 3.76) at the top and proceeds to the experimental $W_2^{5+/4+}$ potential measured in THF shown also in blue at the bottom. In contrast to the gas-phase spectroscopic energy (VIE) that is measured on a fast timescale, the solution potential measures an equilibrium (free energy) that involves the vibrational and thermal enthalpies and entropies of solvated species. These contributions are shown in green in the diagram as obtained from DFT computations (see Experimental Section) where $E_{reorg}$ is the geometric reorganization energy of the positive ion from the structure of the neutral molecule, $\Delta G(v,T)$ includes the differences in zero-point vibrational energies and temperature-dependent $H(T)-TS(T)$ contributions to the free energy at standard temperature and pressure, and $\Delta G_{solv}$ is the solvation stabilization energies of the neutral and cationic species.

The sum of these contributions gives the absolute free energy change for $W_2(hpp)_4/W_2(hpp)_4^+(W_2^{4+/5+})$ in THF of 2.85 eV. A similar calculation for the ferrocene/ferrocene$^+$ couple (Fc/Fc$^+$) gives an absolute free energy change of 5.12 eV, so that the $\Delta G$ for $W_2^{4+/5+}$ is 2.27 eV less than that of Fc/Fc$^+$. Since $\Delta G=-nFE$ and F=1 for the conversion from eV to V, $E_{1/2}$ for $W_2^{4+/5+}$ in THF is calculated to be $-2.27$ V vs. Fc/Fc$^+$. $E_{1/2}$ for the Fc/Fc$^+$ couple consistently occurred at +440 mV vs. Ag/AgCl, so the calculated potential for $W_2(hpp)_4/W_2(hpp)_4^+$ vs. Ag/AgCl is $-1.83$ V. This compares very closely to the observed peak position of $-1.81$ V measured in THF for $W_2(hpp)_4^{2+}$ (TFPB$^-$)$_2$ (TFPB$^-$=tetrakis[3,5-bis(trifluoromethyl)phenyl]borate).

It should be appreciated that the solution reduction potential is determined primarily by two factors. First is the gas-phase vertical ionization energy and second is the solvation stabilization of the positive ion. Because the overall structure of the molecule is largely determined by the structure of the bicyclic guanidinate ligands and their coordination to the metals, and the structure changes little from the neutral to the positive ion, the sum of the reorganization energy and vibrational/thermal contributions shifts the free energy by only about 0.2 eV. Errors in the modeling of these contributions are a small fraction of this number and have little effect on the calculated potential. The good agreement between the calculated and the observed reduction potential then follows primarily from starting with an experimental gas-phase VIE and having a model that gives good account of the $\Delta\Delta G_{solv}$. Nearly all of the models tested were adequate in this regard for these compounds.

The ditungsten tetraguanidinate complexes in the electrochemical studies have chloride atoms coordinated to the tungsten atoms rather than TFPB$^-$ counter ions. Nonetheless the reduction peaks in THF occur at very similar potentials to those of $W_2(hpp)_4^{2+}$(TFPB$^-$)$_2$. A question is the extent to which these dichloro complexes are soluted to ions in THF. The W—Cl interaction is weak as evidenced by the long distance, but the computations indicate that the W—Cl bond is only about one-third electrostatic. Scheme 3 shows the calculated equilibria for dissolution of $W_2(hpp)_4Cl_2$ into ions in THF, along with calculated reduction potentials for various species. The computations indicate that the neutral dichloro complexes are not appreciably soluted to ions in THF, but reduction increasingly favors dissociation of Cl$^-$ from the complex. It is believed that a driving force is the solvation energy of the Cl$^-$ ion in THF ($\Delta G_{solv}$ literature 2.81 eV, DFT calc. 2.91 eV), which also shifts the reduction potential less negative. The DFT calculations estimate the reduction potentials for these complexes too negative and may overestimate the W—Cl bond strength. But even with these overestimates, K in THF ($E_{1/2}$ literature $-2.66$ V, DFT calc. $-2.64$ V) will result in the reduction of $W_2(hpp)_4Cl_2$ to $W_2(hpp)_4$+2Cl$^-$ in THF. The primary driving forces are believed to be the solvation stabilization of the Cl$^-$ ions in comparison to the weak W—Cl interactions and the solvent stabilization of the K$^+$ ions in comparison to the weak stabilization of the $W_2(hpp)_4$ cations in THF.

Scheme 3

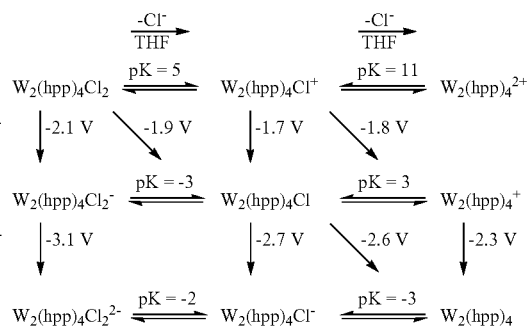

Figure 4:
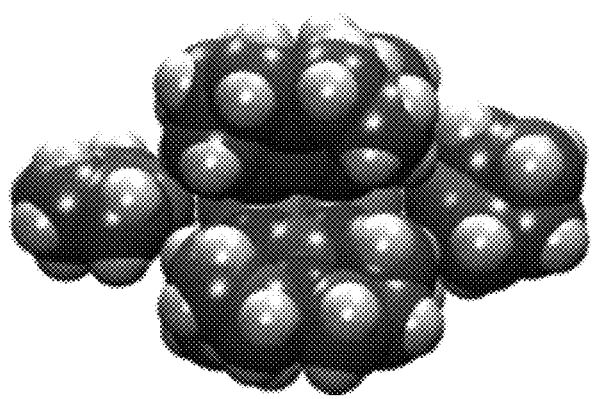
FIG. 4 is an optimized representative structure of $W_2$(hpp)$_4$(THF)$_2^+$ shown with van der Waals atomic radii. The van der Waals contacts impede close association of the THF solvent molecules with the $W_2$ core. Color codes: orange=tungsten; red=oxygen; blue=nitrogen; black=carbon and gray=hydrogen atoms.

One of the possible reasons for the comparatively weak stabilization of the $W_2(hpp)_4^+$ cation in THF, in addition to the size of the molecule, is illustrated in FIG. 4, which shows the optimized structure of the $W_2(hpp)_4$ monocation with THF molecules in the axial sites. It is believed that the van der Waals sizes of the hpp ligands impede the THF oxygen atoms from coming within van der Waals contact with the tungsten atoms, thereby stabilizing the positive charge. In contrast the K$^+$ ion has the advantage of receiving the full stabilization from the THF solvent.

Because the compounds of the invention have the advantage of being soluble in non-polar organic solvents, it is interesting to compare the reducing power of these compounds in non-polar solvents with the hypothetical case of potassium metal in a non-polar solvent. Scheme 4 compares the favorable reduction directions in THF and hexane according to the free energies obtained from this computational model. The equilibrium switches direction from THF to hexane, such that in hexane $W_2(hpp)_4$ reduces K$^+$ to K. Also shown in Scheme 4 is the reducing power of $W_2(hpp)_4$ in comparison to decamethylcobaltocene, a commonly-used strong reducing agent for stoichiometric reactions. As can be seen, $W_2(hpp)_4$ is a much stronger reducing agent than decamethylcobaltocene.

Scheme 4

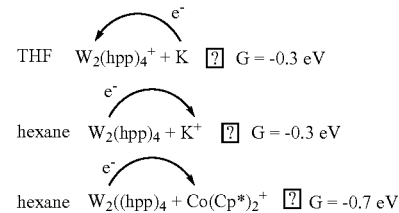

Analogues of the most easily ionized molecule have been prepared in good yields. The ditungsten compounds with four bridging bicyclic guanidinate ligands have very low ionization energies and very negative oxidation potentials. Compounds 3 and 4 are thermally stable and very soluble and stable in non-halogenated, non-protonated solvents such as THF, toluene, benzene and even hexanes. These properties make them ideal candidates for use as strong reducing agents and other wide variety of applications.

Some of the applications of compounds of the invention in the form of catalysts include, but are not limited to, catalysts for hydrocracking, dehalogenation, hydrodesulphurization (HDS), hydrodenitrogenation (HDN) and hydroderomatisation (HAD) of mineral oil products, where tungsten and nickel oxides on ceramic carriers are used; selective catalytic reduction of nitrogen oxides (NOx) (e.g., as catalysts for the removal of nitrogen oxides from stack gases of combustion power plants, chemical plants, cement plants or diesel engines by selective catalytic reduction with ammonia or urea; various applications in the chemical industry, for example dehydrogenation, isomerization, polymerization, reforming, hydration and dehydration, hydroxylation and epoxidation.

Oil, and the gases associated with it, consists of a mixture of hundreds of different hydrocarbons, most of these are straight chain, and saturated hydrocarbons that have little direct use in the chemical industry or as fuel for cars. Thus the various fractions obtained from the distillation of crude oil and the associated gases have to be treated further, sometimes through catalytic reactions in oil refineries, to make them useful. Methods which compounds of the invention, in particular tungsten containing organometallic compounds, provide a high value proposition are in the following exemplary areas: dehydrogenation, aromatization, catalytic reforming Dehydrogenation is a chemical reaction that involves the removal of hydrogen from a molecule. It is the reverse process of hydrogenation. Dehydrogenation processes are used extensively in the oil and gas industry creating, for example, (i) aromatic compounds from raw crude oil to create products, e.g., for increasing fuel octane; and (ii) propylene from the decomposition of propane, which can then be used to produce such organic chemicals as acetone and propylene glycol.

Aromatization is the dehydrogenation and aromatization of paraffins to aromatics. This is the process of converting paraffins obtained from the petroleum distillation process into valuable aromatics. Aromatics created from paraffins can be used to produce high octane gasoline and other refined petro-chemical products.

Catalytic reforming is a chemical process used to convert petroleum refinery naphthals distilled from crude oil (typically having low octane ratings) into high-octane liquid products called reformates, which are premium blending stocks for high-octane gasoline. A large number of reactions occur in catalytic reforming over bifunctional catalysts. Tungsten is used in such reactions as dehydrogenation and dehydroisomerization of naphthenes to aromatics, dehydrogenation of paraffins to olefins, dehydrocyclization of paraffins and olefins to aromatics. Benzene, toluene, xylene and/or ethylbenzene are produced by reformate, the main source of aromatic bulk chemicals. These aromatic compounds are importantly as raw materials for conversion into plastics and other chemicals.

Compounds of the invention can also be used in manufacturing of styrene monomer from dehydrogenation. The conventional method for producing styrene involves two steps: the alkylation of benzene with ethylene to produce ethyl benzene followed by dehydrogenation of the ethyl benzene to produce styrene. Compounds of the invention can be used as catalysts in the dehydrogenation process to produce, for example, styrene which can be used in the fine chemicals, oleochemicals, petrochemicals, and detergents industries. Styrene is used predominately in the production of polystyrene plastics and resins. Styrene is also used as an intermediate in the synthesis of materials used for ion exchange resins and to produce copolymers.

Compounds of the invention can also be used as a catalyst in manufacturing of surfactants in dehydrogenation reaction. Many surfactants are produced through dehydrogenation of linear alkylbenzene. For example, these surfactants are often produced by dehydrogenation of n-paraffins to n-olefins followed by benzene alkylation to produce linear alkylbenzene. The resulting surfactants have improved biodegradability and cost-effectiveness compared to other method of surfactant production.

Compounds of the invention can also be incorporated into thin films. One use is as an n-dopant in electronic and optoelectronic devices. Tungsten is one of a variety of materials known as refractory metals that diffuse slowly, are able to withstand high temperatures, are relatively non-reactive, have low resistance and can be processed to yield thin films on many different substrates. These properties make tungsten containing compounds very useful in the manufacturing of today's high performance integrated circuits (ICs). Physical properties of interest in tungsten films used in semiconductor devices include crystal structure, phase, surface roughness, composition, stress, grain size, crystal orientation, thickness, and adhesion. Most of these physical properties have a direct bearing on the electrical behavior of the tungsten and thus profoundly influence chip performance. In the last two decades, as processor speeds have risen and feature size on semiconductor devices has dropped, some of the more conventional materials used in IC processing have become inadequate for the demands placed upon them. Aluminum is a commonly used material in ICs but has difficulty performing well in new applications. Tungsten is currently most commonly used as a contact material, a conductive diffusion barrier, or as an interconnect between two adjacent metal layers, most commonly called a via.

As discussed herein, compounds of the invention have low ionization energies, and therefore are strong chemical reducing agents. Some of the particular applications of compounds having a low ionization energy include, but are not limited to, emulsion polymerization, vat dyeing, textile stripping and clearing, ground wood bleaching, recycled paper de-inking, precious metal recovery, waste water treatment and iron reduction. Some of the specifically useful applications of compounds of the invention include reduction of nitrogen to ammonia and the reduction of protons to molecular hydrogen. These latter processes are estimated to consume up to 5% of the world's natural gas, require large amounts of energy (e.g., for high temperature and pressure of the reaction), and produce as a side product hundreds of millions of tons of carbon dioxide. Because compounds of the invention are strong reduction catalysts, using compounds of the invention in these processes can eliminate a significant amount of these problems.

Additional objects, advantages, and novel features of this invention will become apparent to those skilled in the art upon examination of the following examples thereof, which are not intended to be limiting. In the Examples, procedures that are constructively reduced to practice are described in the present tense, and procedures that have been carried out in the laboratory are set forth in the past tense.

EXAMPLES

Abbreviations

The following abbreviations are used: DFT, Density Functional Theory; PES, Photoelectron Spectroscopy; DPV, Differential Pulse Voltammetry; hpp, the anion of 1,3,4,6,7,8-hexahydro-2H-pyrimido[1,2-a]pyrimidine; TMhpp, the anion of 3,3,9,9-tetramethyl-1,5,7-triazabicyclo[4.4.0]dec-4-ene; TEhpp=the anion of 3,3,9,9-tetramethyl-1,5,7-triazabicyclo[4.4.0]dec-4-ene; VIE=vertical ionization energy.

Methods and Materials.

All syntheses were carried out under $N_2$ using a Schlenk line equipped with a bubbler with a tube diameter of 2.54 cm and a column of ca. 5 cm of Hg. All manipulations preceding spectroscopic measurements were performed under Argon in a glove box. Commercial solvents were treated as follows: acetonitrile was twice distilled under $N_2$, first from activated molecular sieves and then from $CaH_2$; THF was distilled from Na/K benzophenone; dichloromethane was dried and distilled from $P_4O_{10}$; toluene and isomeric hexanes were dried and degassed using a Glass Contour solvent purification system; o-dichlorobenzene was dried over freshly activated molecular sieves and degassed using vigorous bubbling of $N_2$ immediately before use. Tungsten hexacarbonyl was purchased from commercial sources; HTMhpp and HTEhpp were prepared according to the literature procedures. See, for example, *Polyhedron* 2013, 58, 7-12 and *J. Chem. Phys. B* 2006, 110, 19793-19798.

Instrumentation and Characterization.

$^1$H NMR spectra were recorded on a Mercury 300 spectrometer with chemical shifts referenced to the protonated solvent residue. Mass spectrometry data (electrospray ionization, ESI) were recorded at the Laboratory for Biological Mass Spectrometry at Texas A&M University using an MDS Series Qstar Pulsar with a spray voltage of 5 kV. Elemental analyses were performed by Robertson Microlit Laboratories, Inc., Madison, N.J. on crystalline samples that were previously washed with cold hexanes and dried overnight under vacuum. Infrared spectra were recorded in a Perkin-Elmer 16PC FT IR spectrophotometer using KBr pellets. Electronic spectra were recorded on a Shimadzu UV-2501 PC spectrophotometer. The differential pulse voltammograms were collected using a CH Instruments model-CHI620A electrochemical analyzer in a 0.1 M $Bu^n{}_4NPF_6$ solution in THF, using Pt working and auxiliary electrodes, a Ag/AgCl reference electrode, and a scan rate of 100 mV/s. All potential values are referenced to the Ag/AgCl electrode, and under the present experimental conditions, the $E_{1/2}$ for the $Fc^+/Fc$ couple consistently occurred at +440 mV.

$W_2(TMhpp)_4Cl_2$, 1.

A mixture of 0.240 g (0.682 mmol) of $W(CO)_6$ and 0.300 g (1.53 mmol) of HTMhpp was placed in an oven-dried 100 mL Schlenk flask equipped with a stir bar, and filled with nitrogen. An aliquot of 15 mL of dried and oxygen-free o-dichlorobenzene was then added, and the flask was fitted with a previously oven-dried water-cooled cold finger. The pale yellow reaction mixture was refluxed at 210° C. under nitrogen for 6-8 h. The solvent was removed by pumping under vacuum at 70° C. The greenish-brown solid was extracted with 50 mL of toluene, and the mixture filtered under nitrogen using an oven-dried fritted-glass packed with Celite. The solvent from the green-brown solution was removed under vacuum and the solid washed with hexanes. The solid was dissolved in 10 mL of dichloromethane and the solution was carefully layered with 40 mL of hexanes using a 60 mL Schlenk tube and a glass cap that was wrapped with Parafilm. After four weeks, dark green-brown, block-shaped crystals suitable for X-ray diffraction were obtained. Isolated yield 0.378 g, 91%. $^1$H NMR: ($C_6D_6$, 300 MHz, 25° C.): $\delta_H$=4.17 ppm (s, 16H, 8$CH_2$), 2.63 ppm (s, 16H, 8$CH_2$), and 1.07 ppm (s, 48H, 16$CH_3$). IR (KBr, $cm^{-1}$): ν=2958, 1639, 1530, 1399, 1277, 1125 and 778. UV-vis: $\lambda_{max}$=349.5 nm. ESI-MS: m/z=1179.5, $[W_2(TMhpp)_4Cl]^+$; m/z=572.25, $[W_2(TMhpp)_4]^{2+}$. Electrochemistry in THF vs Ag/AgCl: $E_{1/2}(1)_{THF}$=−0.99 V, $E_{1/2}(2)_{THF}$=−1.84 V. Elemental microanalysis calcd. for $C_{44}H_{80}Cl_2N_{12}W_2$: C, 43.46; H, 6.63; N, 13.82. found: C, 43.40; H, 6.88; N, 13.64. Crystallographic Data for 1.4$CH_2Cl_2$: $M_r$=1555.50, orthorhombic, Pcca, a=24.256(5), b=23.817(5), c=25.791(5) Å, V=14,900(5) Å$^3$, Z=8, $\rho_c$=1.387 Mg m$^{-3}$, T=213(2) K, λ=0.71073 Å. 92163 reflections were collected, 16,921 independent [R(int)=0.0371], which were used in all calculations. $R_1$=0.0270, $wR_2$=0.0609 for observed unique reflections $[F^2>2\sigma(F^2)]$ and $R_1$=0.0631, wR2=0.0677 for all unique reflections. Max. and min. residual electron densities 1.573 and −2.422 eÅ$^{-3}$.

$W_2(TEhpp)_4Cl_2$, 2.

This compound was prepared similarly to 1 using a mixture of 0.240 g (0.682 mmol) of $W_2(CO)_6$ and 0.500 g (1.42 mmol) of HTEhpp in 15 mL of o-dichlorobenzene. After refluxing and removal of the solvent the green-brown solid was extracted with 50 mL of a mixture 4:1 hexanes/toluene and then the mixture was filtered under nitrogen in an oven-dried fitted glass charged with Celite. After the solvent was removed under vacuum from the filtrate, the solid was covered overnight with hexanes at −20° C., and then the supernatant liquid was removed using a cannula. The solid was dissolved in 20 mL of a 4:1 hexanes:toluene mixture. The tube was placed in a refrigerator at −30° C. After four weeks dark green-brown, block-shaped crystals suitable for X-ray diffraction were collected. Isolated yield 0.443 g, 90%. $^1$H NMR: ($C_6D_6$, 300 MHz, 25° C.): $\delta_H$=4.10 pm (s, 16H, 8$CH_2$), 2.81 ppm (s, 16H, 8$CH_2$), 1.49 ppm (q, 32H, 16$CH_2$) and 0.91 ppm. (s, 48H, 16$CH_3$). IR (KBr, $cm^{-1}$): ν=2961, 1637, 1534, 1380, 1275, 1123 and 807. UV-vis: $\lambda_{max}$=347.5 nm. ESI-MS: m/z=1403.7, $[W_2(TEhpp)_4Cl]^+$; m/z=684.4, $[W_2(TEhpp)_4]^{2+}$. Electrochemistry in THF vs Ag/AgCl: $E_{1/2}(1)$=−0.99 V, $E_{1/2}(2)$=−1.90 V. Elemental microanalysis calcd. for $C_{60}H_{112}Cl_2N_{12}W_2$: C, 50.03; H, 7.83; N=11.67. found C, 49.83; H=7.69, N, 11.46. Crystallographic Data for 2: $M_r$=1440.22, monoclinic, $P2_1/c$, a=16.894(4), b=16.778(4), c=22.935(6) Å, β=97.635(5), V=6443(3) Å$^3$, Z=4, $\rho_c$=1.485 Mg m$^{-3}$, T=213(2) K, λ=0.71073 Å. 42958 reflections collected, 14770 independent [R(int)=0.0729], which were used in all calculations. $R_1$=0.0518, $wR_2$=0.0968 for observed unique reflections $[F^2>2\sigma(F^2)]$ and $R_1$=0.1018, wR2=0.1077 for all unique reflections. Max. and min. residual electron densities 2.353 and −1.423 eÅ$^{-3}$.

$W_2(TMhpp)_4$, 3.

A sample of 0.120 g (0.098 mmol) of dark green, solid $W_2(TMhpp)_4Cl_2$, that had been freshly washed with hexanes and then dried under vacuum was placed in a solid addition tube attached to a flask equipped with a stir bar and 0.30 g of freshly cut and cleaned potassium metal in 15 mL of THF. An extremely dry glass frit joined with a side-arm tube served as a cap to the reaction flask. After the solid was added to the flask, the mixture was degassed three times by the freeze pump-thaw method and then heated using a gentle reflux (around 80-85° C.). After 30 min the dark green reaction mixture changed to brown and after 1 h to red-blood. After 2 h of reflux, the reaction mixture was cooled to room temperature and half of the THF was removed under vacuum. The mixture was filtered through the attached fritted glass into a side-armed tube and brought to dryness under vacuum producing a deep-red, solid. Isolated yield 0.081 g, 72%. The solid was dissolved in 10 mL of toluene, set in a Schlenk tube under nitrogen with a glass cap protected with high vacuum grease and wrapped with Parafilm; the stopcocks and all joints were also wrapped with Parafilm and a septum was fitted to the side arm; the tube was placed in a freezer at −30° C. After two weeks, very small dark-red, block-shaped crystals suitable for X-ray diffraction were collected. The product was stored in an ampoule under argon. $^1$H NMR: ($C_6D_6$, 300 MHz, 25° C.): $\delta_H$=3.26 ppm (s, 16H, 8$CH_2$), 2.67 ppm (s, 16H, 8$CH_2$), and 1.15 ppm (s, 48H, 16$CH_3$). $PES_{onset}$: 3.74±0.03 eV. Crystallographic Data for 3: $M_r$=1144.90, triclinic, $P_1^-$, a=10.197(6), b=12.777(8), c=13.452(8) Å, α=112.441(9), β=90.278(10), γ=110.086(10)°, V=1502.6(16) Å$^3$, Z=1, $\rho_c$=1.265 Mg m$^{-3}$, T=213(2) K, λ=0.71073 Å. 9272 reflections collected, 5169 independent [R(int)=0.0871], which were used in all calculations. $R_1$=0.0862, w$R_2$=0.1562 for observed unique reflections [$F^2$>2σ($F^2$)] and $R_1$=0.1541, wR2=0.1744 for all unique reflections. Max. and min. residual electron densities 5.483 and −2.426 eÅ$^{-3}$.

$W_2(TEhpp)_4$, 4.

This compound was prepared similarly to 3 using 0.14 g, 0.097 mmol of dark green solid $W_2(TEhpp)_4Cl_2$, 0.3 g of clean potassium metal and 15 mL of THF. After refluxing and filtration of the deep red reaction mixture, the solvent was removed to produce 0.095 g of a deep red solid. Isolated yield 0.095 g, 71%. The product was stored in a sealed ampoule under argon. $^1$H NMR: ($C_6D_6$, 300 MHz, 25° C.): $\delta_H$=3.48 ppm (s, 16H, 8$CH_2$), 2.73 ppm (s, 16H, 8$CH_2$), 1.70 ppm (q, 16H, 8$CH_2$), 1.46 ppm (q, 16H, 8$CH_2$) and 0.92 ppm (s, 48H, 16$CH_3$). $PES_{vertical}$: 3.71±0.03 eV.

Photoelectron Spectroscopy (PES).

The gas-phase PES of $W_2(TMhpp)_4$ and $W_2(TEhpp)_4$ were recorded using an instrument that features a 36-cm radius, 8-cm gap hemispherical analyzer, and custom-designed excitation source, sample cells, detection and control electronics, and methods that have been described, for example, in *Rev. Sci. Instrum.* 1986, 57, 2366 and *J. Am. Chem. Soc.* 1998, 120, 3382-3386. The temperature was monitored using a "K"-type thermocouple passed through a vacuum feed through and attached directly to the sample cell. Samples of $W_2(TMhpp)_4$ and $W_2(TEhpp)_4$ were loaded into stainless steel cells and placed in the instrument using rigorous air-sensitive techniques. The data collection focused on determining the δ bond ionization energy. To avoid decomposition in the sample chamber of the cell, ampoules containing the samples were broken off and placed directly in the ionization chamber.

The $W_2(TMhpp)_4$ sample began to sublime at 216° C. and data was collected continually with gradually increasing temperature until 271° C. when the loaded sample was fully consumed. Complete spectra were collected every few minutes. The sample lasted for ca. 2½ h in the chamber without evidence of decomposition. The individual spectral scans showed the same ionization features, and the displayed spectra are the sum of the individual scans. Sublimation of the $W_2(TEhpp)_4$ sample began at around 317° C. and was still present at 340° C. The signal was observed for about 1 h again without evidence of decomposition, and the displayed spectrum is the sum of the individual scans.

The $^2P_{3/2}$ peak of argon at 15.76 eV ionization energy is typically used for internal energy calibration, but over the course of the experiment sensitivity to the $^2P_{3/2}$ peak of Ar was lost. This often happens with molecules that are strong reductants, presumably because of the very large change in work function of the spectrometer when the sample condenses on the spectrometer surfaces. At this point the lamp was adjusted to emit He II photons in addition to He I photons. This allowed observation of the He self-ionization (by He II photons) at an apparent binding energy of 4.99 eV in the He I spectrum. This very sharp line is a convenient internal energy calibrant and is preferable for the calibration of low-energy ionizations. The resolution, as measured by the Ar peak before it was no longer visible, was approximately 0.030 eV. The resolution for the $W_2(TMhpp)_4$ and $W_2(TEhpp)_4$ experiments, as measured by the He self-ionization, was 71 meV and 88 meV, respectively. Over the course of two separate data collections of $W_2(TMhpp)_4$, approximately 800 counts of the full He I spectrum (Graphic S1) and an additional 400 counts of a close-up on the δ bond ionization were collected. For $W_2(TEhpp)_4$ approximately 400 counts of the δ bond ionization were collected.

The ionization bands are represented analytically with asymmetric Gaussian peaks. As is typical for the first ionization bands of $M_2(hpp)_4$ molecules, a weak shoulder is observed on the high ionization energy side of the peak that necessitates the use of a second asymmetric Gaussian component to reasonably account for the total contour of the ionization intensity. The additional ionization intensity on the high ionization energy side of the first band is ascribed to the different puckered conformations that the hpp ligands can adopt in the molecules. The relative intensity of this component varies among the different $M_2hpp_4$ molecules. The broadening on the high ionization energy side of the $W_2(TEhpp)_4$ ionization is the greatest, where additional conformations due to the ethyl group orientations are possible. The vertical ionization energies are reported as the position of the main Gaussian peak in the analytical representation. The onset of ionization is the position at which the observed electron counts are significantly above a linear baseline through the peak.

Crystallographic data for 1, 2 and 3.

Crystals were coated with Paratone oil and mounted on a nylon Cryoloop affixed to a goniometer head. Data were collected at 213 K on a Bruker SMART 1000 CCD area detector system using omega scans of 0.3 deg/frame, with exposures of 60 (1), 50 (2) and 80 (3) seconds per frame, such that 1271 frames were collected for a full hemisphere of data. For each compound, the first 50 frames were collected again at the end of the data collection to monitor for crystal decay. No significant decomposition was observed. Cell parameters were determined using the program SMART. Data reduction and integration were performed with the software package SAINT, which corrects for Lorentz and polarization effects, while absorption corrections were applied by using the program SADABS.

The structures were initially determined using the program XPREP from the SHELX software package. Compound 1 was identified as belonging to the orthorhombic space group Pcca by its systematic absences. Because of residual disorder in solvent molecules, the Squeeze tool from Platon software was applied to finish the structure refinement. The structure contains two independent molecules in the asymmetric unit which means there are eight molecules per unit cell. Compound 2 gave a good refinement in the monoclinic space group P2$_1$/c. For this compound no interstitial solvent was found; there is one molecule in the asymmetric unit and four in the unit cell. Compound 3 was refined, following the Marsh's recommendation of choose the higher symmetry group, in the triclinic space group $P_1^-$ instead of the non-centrosymmetric P1 that was the first choice suggested by the XPREP program; there is only one molecule in the asymmetric and unit cell. The methyl groups from the TMhpp ligands were disordered where the major components having occupancies between 50.3 and 54.2%. The structure contained interstitial disordered solvent that was treated using the Squeeze tool from the Platon software.

Computational Model.

Several density functional and basis set models were tested for their ability to account for the geometric structures and first gas-phase ionization energies of this class of ditungsten complexes. As pointed out in the discussion these features are the most important in relation to the reduction chemistry of these complexes. Functionals were tested at the level of the local density approximation (LDA), the generalized gradient approximation (GGA) with and without dispersion corrections, meta-GGA, hybrid, and meta-hybrid. Selected results with the Amsterdam Density Functional program version adf2013.01 are shown in the SI. All functionals overestimated the W—W bond length by about 0.05 Å and underestimated the first ionization energy by as much as 0.6 eV. The LDA and GGA functionals had difficulty modeling the length of the weak W—Cl bonds, and the breaking of these bonds with reduction is important in the synthesis depicted in Scheme 1. Inclusion of dispersion with BJ damping with the PBE functional (PBE-D3) gave geometries that compared generally as well with the experimental W—Cl distance as the familiar meta-GGA and hybrid functionals, and gave a somewhat better first ionization energy at much less computational cost, and therefore this model was selected for the remaining computations. The basis set selected for the geometry optimizations and electronic energies was double-zeta valence for hydrogen (DZ) and triple-zeta valence plus polarization (TZP, with non-valence core) for all other atoms but tungsten. For tungsten an additional polarization function was added (TZ2P) to minimize basis set superposition errors (BSSE) for Cl$^-$ dissociation with reduction, but as shown below BSSE is not a concern for this study because of the modeling approach. Relativistic effects are included by the Zero Order Regular Approximation (ZORA). Solvation free energies are estimated by the Conductor like Screening Model (COSMO) of solvation using default parameters.

Zero-point vibrational energies and thermal contributions to the free energy are computed at a lower level of theory because these terms have small contributions to the reduction chemistry for these complexes, and to save computational costs. The functional was the Vosko-Wilk-Nusair LDA with Stoll's correction and the basis set was TZP for tungsten and DZ for all other atoms. Harmonic vibrational frequencies were calculated analytically and used without scaling to calculate the gas phase zero-point energies and thermal vibrational enthalpies and entropies. It is known that the gas-phase translational and rotational entropies overestimate the entropies in solution, and this is especially a problem when the number of reactant molecules is different from the number of product molecules. The gas-phase translational and rotational entropies were scaled by 0.5 in solution similar to other adjustments in the literature. This uncertainty was further mitigated by explicitly including solvent molecules to balance the number of reactant and product molecules. For example, for the release of the Cl$^-$ ion with reduction, the vacated W$_2$ axial coordination site was made to be occupied with a THF molecule. This had the additional advantages of 1) the basis set superposition error of a vacant site was eliminated, and 2) the explicit energy interaction of the THF molecule in the inner sphere in combination with the continuum solvation model for the outer sphere gave a better determination of the solvation energy.

The foregoing discussion of the invention has been presented for purposes of illustration and description. The foregoing is not intended to limit the invention to the form or forms disclosed herein. Although the description of the invention has included description of one or more embodiments and certain variations and modifications, other variations and modifications are within the scope of the invention, e.g., as may be within the skill and knowledge of those in the art, after understanding the present disclosure. It is intended to obtain rights which include alternative embodiments to the extent permitted, including alternate, interchangeable and/or equivalent structures, functions, ranges or steps to those claimed, whether or not such alternate, interchangeable and/or equivalent structures, functions, ranges or steps are disclosed herein, and without intending to publicly dedicate any patentable subject matter. All references cited herein are incorporated by reference in their entirety.

What is claimed is:

1. A thin film comprising a compound of the formula: $M_a(L)_bX_c$, wherein each M is independently tungsten or chromium; each L is independently a bicyclic heterocyclic anionic compound; X is a halide; a is 1 or 2; b is an integer from 1 to 4; and c is an integer from 0 to 2, and wherein said solid crystal has an onset ionization energy of about 4 eV or less and is soluble in an organic solvent.

2. The thin film of claim 1, wherein said compound is soluble in an aprotic organic solvent.

3. The thin film of claim 1, wherein said compound is soluble in a nonpolar organic solvent.

4. The thin film of claim 1, wherein said compound has an oxidation potential in THF of about −1.5 V or less.

5. The thin film of claim 4, wherein said compound has an oxidation potential in THF of about −1.8 V or less.

6. The thin film of claim 1, wherein said compound has an onset ionization energy of about 3.6 eV or less.

7. The substrate of claim 1, wherein the solubility of said compound in THF is at least 0.1 g/L.

8. The thin film of claim 7, wherein the solubility of said compound in THF is at least 1 g/L.

9. The thin film of claim 1, wherein the solubility of said compound in benzene is at least 0.1 g/L.

10. The thin film of claim 7, wherein the solubility of said compound in benzene is at least 1 g/L.

11. An integrated circuit comprising a compound of the formula: $M_a(L)_bX_c$, wherein each M is independently tungsten or chromium; each L is independently a bicyclic heterocyclic anionic compound; X is a halide; a is 1 or 2; b is an integer from 1 to 4; and c is an integer from 0 to 2, and wherein said compound has an oxidation potential in THF of about −1.5 V or less, and is soluble in an organic solvent.

12. The integrated circuit of claim 11, wherein said compound has an oxidation potential in THF of about −1.8 V or less.

13. The integrated circuit of claim 11, wherein said compound has an onset ionization energy of about 4 eV or less.

14. The integrated circuit of claim 13, wherein said compound has an onset ionization energy of about 3.6 eV or less.

15. A compound of the formula:

$$M_a(L)_bX_c$$

wherein
each M is independently tungsten or chromium;
each L is independently a bicyclic heterocyclic anionic compound;

X is a halide;
a is 1 or 2;
b is an integer from 1 to 4; and
c is an integer from 0 to 2.

16. The compound of claim 15, wherein said bicyclic heterocyclic anionic compound is of the formula:

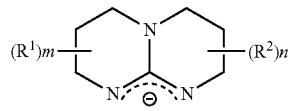

wherein
each of m and n is independently an integer from 0 to 4, provided the sum of m and n is at least 1; and
each of $R^1$ and $R^2$ is independently alkyl.

17. The compound of claim 16, wherein $R^1$ and $R^2$ are independently methyl, or ethyl.

18. The compound of claim 16, wherein m is 2.

19. The compound of claim 16, wherein n is 2.

20. The compound of claim 16, wherein said compound is of the formula:

$$M_2(L)_4Xc$$

wherein
M and X are those defined in claim 15;
L is that defined in claim 16; and
c is an integer of 0 or 2.

* * * * *